(12) United States Patent
Ito (10) Patent No.: US 12,150,844 B2
(45) Date of Patent: Nov. 26, 2024

(54) WATER ABSORBENT RESIN PARTICLES

(71) Applicant: SUMITOMO SEIKA CHEMICALS CO., LTD., Hyogo (JP)

(72) Inventor: Takashi Ito, Himeji (JP)

(73) Assignee: SUMITOMO SEIKA CHEMICALS CO., LTD., Hyogo (JP)

( * ) Notice: Subject to any disclaimer, the term of this patent is extended or adjusted under 35 U.S.C. 154(b) by 672 days.

(21) Appl. No.: 17/311,907

(22) PCT Filed: Dec. 12, 2019

(86) PCT No.: PCT/JP2019/048808
§ 371 (c)(1),
(2) Date: Jun. 8, 2021

(87) PCT Pub. No.: WO2020/122209
PCT Pub. Date: Jun. 18, 2020

(65) Prior Publication Data
US 2022/0023114 A1    Jan. 27, 2022

(30) Foreign Application Priority Data

Dec. 12, 2018  (JP) ................................ 2018-232724
Dec. 12, 2018  (JP) ................................ 2018-232726
(Continued)

(51) Int. Cl.
*C08F 20/06*  (2006.01)
*A61F 13/539*  (2006.01)
(Continued)

(52) U.S. Cl.
CPC ............ *A61F 13/539* (2013.01); *A61L 15/24* (2013.01); *B01J 20/267* (2013.01);
(Continued)

(58) Field of Classification Search
None
See application file for complete search history.

(56) References Cited

U.S. PATENT DOCUMENTS

2019/0111411 A1*  4/2019  Torii ....................... A61L 15/60
2019/0276609 A1    9/2019  Lee et al.

FOREIGN PATENT DOCUMENTS

CN    101808728    8/2010
CN    104507565    4/2015
(Continued)

OTHER PUBLICATIONS

International Preliminary Report on Patentability of PCT/JP2019/048808, Jun. 24, 2021, 10 pages.
(Continued)

*Primary Examiner* — Richard A. Huhn
(74) *Attorney, Agent, or Firm* — HSML P.C.

(57) ABSTRACT

Disclosed is water-absorbent resin particles including: a crosslinked polymer having a monomer unit derived from an ethylenically unsaturated monomer including at least one compound selected from the group consisting of (meth) acrylic acid and a salt thereof, in which a proportion of (meth)acrylic acid and a salt thereof is 70 to 100 mol % with respect to a total amount of monomer units in the crosslinked polymer, an artificial urine permeation speed when the water-absorbent resin particles are swollen tenfold is 1.0 g/min or more and 35.0 g/min or less, a water retention capacity for a physiological saline solution is 32 to 60 g/g, and a contact angle measured in a test performed in the order of i) and ii) is 70 degrees or smaller.

7 Claims, 3 Drawing Sheets

(30) Foreign Application Priority Data

| Dec. 12, 2018 | (JP) | 2018-232728 |
| Dec. 12, 2018 | (JP) | 2018-232843 |
| Dec. 12, 2018 | (JP) | 2018-232847 |
| Dec. 12, 2018 | (JP) | 2018-232848 |
| Dec. 12, 2018 | (JP) | 2018-232850 |
| Dec. 12, 2018 | (JP) | 2018-232851 |
| Dec. 12, 2018 | (JP) | 2018-232856 |
| Dec. 12, 2018 | (JP) | 2018-232857 |
| Jan. 30, 2019 | (JP) | 2019-014522 |
| Mar. 22, 2019 | (JP) | 2019-055281 |

(51) Int. Cl.
- A61L 15/24 (2006.01)
- B01J 20/26 (2006.01)
- B01J 20/28 (2006.01)
- A61F 13/53 (2006.01)

(52) U.S. Cl.
CPC ... *B01J 20/28004* (2013.01); *B01J 20/28016* (2013.01); *A61F 2013/530569* (2013.01); *A61F 2013/530591* (2013.01); *A61F 2013/530729* (2013.01); *A61F 2013/53908* (2013.01); *C08F 20/06* (2013.01)

(56) References Cited

FOREIGN PATENT DOCUMENTS

| EP | 0761241 | 3/1997 |
| EP | 1813628 | 8/2007 |
| EP | 2893974 | 7/2015 |
| EP | 3153529 | 4/2017 |
| EP | 3168241 | 5/2017 |
| EP | 3437732 | 2/2019 |
| EP | 3521376 | 8/2019 |
| JP | H9-124955 | 5/1997 |
| JP | H9-509343 | 9/1997 |
| JP | H9-509592 | 9/1997 |
| JP | H11-071425 | 3/1999 |
| JP | H11-080248 | 3/1999 |
| JP | 2003-088552 | 3/2003 |
| JP | 2004-261797 | 9/2004 |
| JP | 2005-097519 | 4/2005 |
| JP | 2005-111474 | 4/2005 |
| JP | 2006-068731 | 3/2006 |
| JP | 2010-241975 | 10/2010 |
| JP | 2010-540206 | 12/2010 |
| JP | 2014-005472 | 1/2014 |
| JP | 2018-181565 | 11/2018 |
| KR | 10-2018-0092661 | 8/2018 |
| WO | 95/022355 | 8/1995 |
| WO | 95/022357 | 8/1995 |
| WO | 2004/069293 | 8/2004 |
| WO | 2004/069915 | 8/2004 |
| WO | 2005/027986 | 3/2005 |
| WO | 2005/075070 | 8/2005 |
| WO | 2006/014031 | 2/2006 |
| WO | 2009/041727 | 4/2009 |
| WO | 2011/126079 | 10/2011 |
| WO | 2016/148153 | 9/2016 |
| WO | 2017/170605 | 10/2017 |
| WO | WO-2017170605 A1 * | 10/2017 ............. A61F 13/53 |
| WO | 2018/062539 | 4/2018 |
| WO | 2018/159800 | 9/2018 |
| WO | 2018/181565 | 10/2018 |

OTHER PUBLICATIONS

International Search Report of PCT/JP2019/048808, Mar. 17, 2020, 3 pages.

"Certificate of Experimental Results Opponent's Exhibit No. 11", submitted for Japanese Patent Application No. 2019-055281, Oct. 15, 2020, 6 pages; English translation provided.

"Certificate of Experimental Results Opponent's Exhibit No. 12", submitted for Japanese Patent Application No. 2019-055281, Oct. 15, 2020, 6 pages; English translation provided.

"Certificate of Experimental Results Opponent's Exhibit No. 13", submitted for Japanese Patent Application No. 2019-055281, Oct. 15, 2020, 6 pages; English translation provided.

"Certificate of Experimental Results Opponent's Exhibit No. 14", submitted for Japanese Patent Application No. 2019-055281, Oct. 15, 2020, 6 pages; English translation provided.

"Certificate of Experimental Results Opponent's Exhibit No. 15", submitted for Japanese Patent Application No. 2019-055281, Oct. 15, 2020, 6 pages; English translation provided.

"Certificate of Experimental Results Opponent's Exhibit No. 16 ", submitted for Japanese Patent Application No. 2019-055281, Oct. 15, 2020, 7 pages; English translation provided.

"Certificate of Experimental Results Opponent's Exhibit No. 17", submitted for Japanese Patent Application No. 2019-055281, Oct. 15, 2020, 6 pages; English translation provided.

Notice of reasons for cancellation issued for Japanese Patent Application No. 2019-055281 (Patent No. 6681494), mailed on Dec. 23, 2020, 112 pages; English translation provided.

Notice of reasons for cancellation issued for Japanese Patent Application No. 2019-055281 (Patent No. 6681494), mailed on Jun. 17, 2021, 32 pages; English translation provided.

Fredric L. Buchholz, Andrew T. Graham, "Modern Superabsorbent Polymer Technology", 1998, pp. 167 and 187-190.

"Certificate of Experimental Results", submitted for Japanese Patent Application No. 2019-055281, Jun. 17, 2021, 6 pages; English translation provided.

"A picture that the contact angle is 35 degrees in the measurement of the contact angle n = 5 in Exhibit A No. 1.", Jun. 17, 2021, 2 pages; English translation provided.

"Patent technology status and development trend of super absorbent resin for sanitary use", 2012-2013, p. 317; with English translation.

The extended European search report issued for European Patent Application No. 19896038.7, Sep. 29, 2022, 8 pages.

* cited by examiner

WATER ABSORBENT RESIN PARTICLES

TECHNICAL FIELD

The present invention relates to water-absorbent resin particles.

BACKGROUND ART

A water-absorbent resin is used in the field of sanitary products. Specifically, it is used as a material for an absorbent contained in an absorbent article such as a diaper. For example, Patent Literature 1 discloses water-absorbent resin particles having a specific absorption speed pattern measured by a DW method, and a method for producing the same, and discloses that an absorbent article to which the water-absorbent resin particles are applied has an unbiased absorption rate, and has an excellent amount of absorption and absorption speed.

CITATION LIST

Patent Literature

[Patent Literature 1] JP 2014-5472 A

SUMMARY OF INVENTION

Technical Problem

Since an absorbent article such as diapers is directly brought into contact with the skin when it is used, it is preferable that moisture do not stay on the surface of the absorbent article after it absorbs a liquid so that it dries quickly and thereby imparts a dry and soft sensation. However, water-absorbent resin particles that provide an absorbent article having such properties to a sufficient level have not been obtained.

An object of the present invention is to provide water-absorbent resin particles from which a dry and soft sensation can be quickly obtained after they absorb water when they are used for sanitary products.

Solution to Problem

Water-absorbent resin particles of the present invention, in which an artificial urine permeation speed when the water-absorbent resin particles are swollen tenfold is 1.0 g/min or more, and a contact angle measured in a test performed in the order of i) and ii) below is 70 degrees or smaller, is provided.
  i) A spherical liquid droplet, which corresponds to a diameter of 3.0±0.1 mm, of a 25% by mass saline solution is added dropwise at 25° C. onto a surface of a layer formed from the water-absorbent resin particles to bring the water-absorbent resin particles into contact with the liquid droplet.
  ii) A contact angle of the liquid droplet is measured at a timing which is 30 seconds after the liquid droplet is brought into contact with the surface.

The above water-absorbent resin particles may have a water retention capacity for a physiological saline solution of 20 to 60 g/g.

The above water-absorbent resin particles may have a water absorption capacity for a physiological saline solution under a load of 4.14 kPa of 15 ml/g or more.

Advantageous Effects of Invention

According to the present invention, water-absorbent resin particles, from which a dry and soft sensation can be quickly obtained after they absorb water when they are used for sanitary products, are provided.

DESCRIPTION OF EMBODIMENTS

Hereinafter, suitable embodiments of the present invention will be described in detail. However, the present invention is not limited to the following embodiments.

In the present specification, "acrylic" and "methacrylic" are collectively referred to as "(meth)acrylic." "Acrylate" and "methacrylate" are also referred to as "(meth)acrylate." Regarding numerical value ranges described in a stepwise manner in the present specification, an upper limit value or a lower limit value of a numerical value range in a certain step can be arbitrarily combined with an upper limit value or a lower limit value of a numerical value range in another step. In a numerical value range described in the present specification, an upper limit value or a lower limit value of the numerical value range may be replaced with a value shown in examples. The term "water-soluble" means that a solubility of 5% by mass or more is exhibited in water at 25° C. For materials exemplified in the present specification, one kind may be used alone, or two or more kinds may be used in combination. In a case where there are a plurality of substances corresponding to each of components in a composition, a content of each of the components in the composition means a total amount of the plurality of substances present in the composition unless otherwise specified.

Water-absorbent resin particles according to the present embodiment have an artificial urine permeation speed of 1.0 g/min or more when they are swollen tenfold. An artificial urine permeation speed when the water-absorbent resin particles are swollen tenfold may be 1.5 g/min or more, 2.0 g/min or more, or 3.0 g/min or more, from the viewpoint of further enhancing the effect of the present invention. An artificial urine permeation speed when the water-absorbent resin particles are swollen tenfold may be 35.0 g/min or less, and is preferably 30.0 g/min or less. Furthermore, an artificial urine permeation speed when the water-absorbent resin particles are swollen tenfold may be 20.0 g/min or less, 15.0 g/min or less, or 12.5 g/min or less. The artificial urine permeation speed when the water-absorbent resin particles are swollen tenfold is defined as a value measured by a method described in Examples to be described later. In the present specification, the artificial urine is an aqueous solution consisting of 0.780% by mass of sodium chloride, 0.022% by mass of calcium chloride, 0.038% by mass of magnesium sulfate, 0.002% by mass of Blue No. 1, and water.

A contact angle of the water-absorbent resin particles according to the present embodiment which is measured in a test performed in the order of i) and ii) below is 70 degrees or smaller.

i) A spherical liquid droplet, which corresponds to a diameter of 3.0±0.1 mm, of a 25% by mass saline solution is added dropwise at 25° C. onto a surface of a layer formed from the water-absorbent resin particles to bring the water-absorbent resin particles into contact with the liquid droplet.

ii) A contact angle of the liquid droplet is measured at a timing which is 30 seconds after the liquid droplet is brought into contact with the surface.

A contact angle may be 65 degrees or smaller, 55 degrees or smaller, or 45 degrees or smaller, from the viewpoint of further enhancing the effect of the present invention. Furthermore, a contact angle may be 0 degrees or larger, larger than 0 degrees, 10 degrees or larger, or 20 degrees or larger. A contact angle is preferably 30 degrees or larger.

The contact angle is a value measured according to "Testing Method Of Wettability Of Glass Substrate Surface" in JIS R 3257 (1999). Specifically, it is measured by a method described in Examples to be described later.

When the artificial urine permeation speed when the water-absorbent resin particles are swollen tenfold and the contact angle are within predetermined ranges, the water-absorbent resin particles according to the present embodiment quickly draw water after they absorb water when they are used for sanitary products, and thereby they can promptly impart a dry and soft sensation on the surface of an absorbent article. The water-absorbent resin particles according to the present embodiment have sufficiently high hydrophilicity on the surface of the particles and are excellent in wettability, and therefore have an excellent ability to draw water into the particles.

The water-absorbent resin particles according to the present embodiment can have a high water absorption capacity with respect to a physiological saline solution. A water retention capacity of the water-absorbent resin particles according to the present embodiment for a physiological saline solution may be, for example, 20 g/g or more, 25 g/g or more, 27 g/g or more, 30 g/g or more, 32 g/g or more, 35 g/g or more, 37 g/g or more, 39 g/g or more, or 40 g/g or more, from the viewpoint of appropriately increasing an absorption capacity of an absorbent. A water retention capacity of the water-absorbent resin particles for a physiological saline solution may be 60 g/g or less, 57 g/g or less, 55 g/g or less, 52 g/g or less, 50 g/g or less, 47 g/g or less, 45 g/g or less, 43 g/g, or 42 g/g or less. A water retention capacity for a physiological saline solution may be 20 to 60 g/g, 25 to 55 g/g, 25 to 50 g/g, 25 to 45 g/g, 30 to 45 g/g, or 32 to 42 g/g. Furthermore, a water retention capacity for a physiological saline solution may be 32 to 60 g/g, 35 to 60 g/g, 37 to 60 g/g, 39 to 60 g/g, 39 to 55 g/g, 40 to 55 g/g, 40 to 52 g/g, or 40 to 50 g/g. The water retention capacity for a physiological saline solution is measured by a method described in Examples to be described later.

A water absorption capacity of the water-absorbent resin particles according to the present embodiment for a physiological saline solution under a load of 4.14 kPa (0.6 psi) (water absorption capacity under a load) may be, for example, 15 ml/g or more, 18 ml/g or more, or 20 ml/g or more. A water absorption capacity for a physiological saline solution under a load of 4.14 kPa may be, for example, 35 ml/g or less, or 30 ml/g or less. The water absorption capacity for a physiological saline solution under a load of 4.14 kPa is measured by a method described in Examples to be described later.

Examples of shapes of the water-absorbent resin particles according to the present embodiment include a substantially spherical shape, a crushed shape, and a granular shape. A median particle size of the water-absorbent resin particles according to the present embodiment may be 250 to 850 μm, 300 to 700 μm, or 300 to 600 μm. The water-absorbent resin particles according to the present embodiment may have a desired particle size distribution at a timing at which polymer particles are obtained by a production method to be described later, but their particle size distribution may be adjusted by performing operations such as adjustment of a particle size through classification with a sieve.

A water absorption speed of the water-absorbent resin particles according to the present embodiment for a physiological saline solution may be, for example, 20 to 80 seconds, 25 to 70 seconds, or 30 to 60 seconds. The water absorption speed for a physiological saline solution is measured by the following method. In a room adjusted to 25° C.±1° C., 50±0.1 g of a physiological saline solution that has been put into a beaker having a capacity of 100 ml is adjusted to a temperature of 25° C.±0.2° C. in a thermostatic water bath, and then stirred at 600 rpm with a magnetic stirrer bar (8 mmφ×30 mm, without a ring) to generate a vortex. 2.0±0.002 g of the water-absorbent resin particles is added into the above physiological saline solution at once, and a time (sec) until the vortex disappears and the liquid surface becomes flat after the addition of the water-absorbent resin particles is measured. The time is taken as a water absorption speed of the water-absorbent resin particles for a physiological saline solution.

The water-absorbent resin particles according to the present embodiment can contain, for example, a crosslinked polymer formed by polymerization of monomers including ethylenically unsaturated monomers. The crosslinked polymer has a monomer unit derived from an ethylenically unsaturated monomer. That is, the water-absorbent resin particles according to the present embodiment can have a structural unit derived from ethylenically unsaturated monomers.

Examples of methods for polymerizing the monomers include a reverse-phase suspension polymerization method, an aqueous solution polymerization method, a bulk polymerization method, and a precipitation polymerization method. Among them, the reverse-phase suspension polymerization method or the aqueous solution polymerization method is preferable from the viewpoints of facilitating securement of favorable water absorption characteristics of the obtained water-absorbent resin particles and control of a polymerization reaction. Hereinbelow, a method for polymerizing ethylenically unsaturated monomers will be described with the reverse-phase suspension polymerization method as an example.

An ethylenically unsaturated monomer is preferably water-soluble. Examples thereof include (meth)acrylic acid and a salt thereof, 2-(meth)acrylamide-2-methylpropanesulfonic acid and a salt thereof, (meth)acrylamide, N,N-dimethyl (meth)acrylamide, 2-hydroxyethyl (meth)acrylate, N-methylol (meth)acrylamide, polyethylene glycol mono (meth)acrylate, N,N-diethylaminoethyl (meth)acrylate, N,N-diethylaminopropyl (meth)acrylate, and diethylaminopropyl (meth)acrylamide. In a case where an ethylenically unsaturated monomer has an amino group, the amino group may be quaternarized. A functional group such as a carboxyl group and an amino group, which is contained in the monomer, can function as a crosslinkable functional group in a surface crosslinking process to be described later. These ethylenically unsaturated monomers may be used alone or in a combination of two or more kinds thereof.

Among them, from the viewpoint of high industrial availability, the ethylenically unsaturated monomer preferably includes at least one compound selected from the group consisting of (meth)acrylic acid and a salt thereof, acrylamide, methacrylamide, and N,N-dimethyl acrylamide, and more preferably includes at least one compound selected from the group consisting of (meth)acrylic acid and a salt thereof, and acrylamide. The ethylenically unsaturated monomer more preferably includes at least one compound selected from the group consisting of (meth)acrylic acid and a salt thereof from the viewpoint of further enhancing water absorption characteristics.

For the monomer, a monomer other than the above-mentioned ethylenically unsaturated monomers may be partially used. Such a monomer can be used by, for example, being mixed with an aqueous solution containing the ethylenically unsaturated monomers. A usage amount of the ethylenically unsaturated monomers may be, for example, 70 to 100 mol %, may be 80 to 100 mol %, may be 90 to 100 mol %, may be 95 to 100 mol %, or may be 100 mol %, with respect to a total amount of monomers. Among them, a proportion of (meth)acrylic acid and a salt thereof may be 70 to 100 mol %, may be 80 to 100 mol %, may be 90 to 100 mol %, may be 95 to 100 mol %, or may be 100 mol %, with respect to a total amount of monomers.

Usually, the ethylenically unsaturated monomers are suitably used in a form of an aqueous solution. In general, it is sufficient for a concentration of the ethylenically unsaturated monomers in an aqueous solution containing the ethylenically unsaturated monomers (hereinafter, referred to as an aqueous solution of monomers) to be 20% by mass or more and a saturated concentration or less, and it is preferably 25% to 70% by mass, and is more preferably 30% to 55% by mass. Examples of water to be used include tap water, distilled water, and ion exchange water.

In a case where ethylenically unsaturated monomers to be used have an acidic group, an aqueous solution of monomers may be used after neutralizing this acidic group with an alkaline neutralizing agent. From the viewpoint of increasing an osmotic pressure of the obtained water-absorbent resin particles and thereby further enhancing water absorption characteristics such as a water retention capacity, a degree of neutralization in the ethylenically unsaturated monomers by the alkaline neutralizing agent is 10 to 100 mol %, is preferably 50 to 90 mol %, and is more preferably 60 to 80 mol % of the acidic group in the ethylenically unsaturated monomers. Examples of alkaline neutralizing agents include alkali metal salts such as sodium hydroxide, sodium carbonate, sodium hydrogen carbonate, potassium hydroxide, and potassium carbonate; and ammonia. These alkaline neutralizing agents may be used in a form of an aqueous solution to simplify a neutralizing operation. The above-mentioned alkaline neutralizing agents may be used alone or in combination of two or more kinds thereof. Neutralization of the acidic groups in the ethylenically unsaturated monomers can be performed by, for example, adding an aqueous solution of sodium hydroxide, potassium hydroxide, or the like dropwise to the aqueous solution of monomers and mixing them.

In the reverse-phase suspension polymerization method, an aqueous solution of monomers is dispersed in a hydrocarbon dispersion medium in the presence of a surfactant, and polymerization of ethylenically unsaturated monomers is performed using a radical polymerization initiator or the like.

Examples of surfactants include nonionic surfactants and anionic surfactants. Examples of nonionic surfactants include sorbitan fatty acid esters, (poly)glycerin fatty acid esters (where "(poly)" means both of a case with the prefix "poly" and a case without the prefix "poly," and the same applies hereinbelow), sucrose fatty acid esters, polyoxyethylene sorbitan fatty acid esters, polyoxyethylene glycerin fatty acid esters, sorbitol fatty acid esters, polyoxyethylene sorbitol fatty acid esters, polyoxyethylene alkyl ethers, polyoxyethylene alkylphenyl ethers, polyoxyethylene castor oil, polyoxyethylene hydrogenated castor oil, alkylallyl formaldehyde condensed polyoxyethylene ethers, polyoxyethylene polyoxypropylene block copolymers, polyoxyethylene polyoxypropyl alkyl ethers, and polyethylene glycol fatty acid esters. Examples of anionic surfactants include fatty acid salts, alkylbenzene sulfonate, alkyl methyl taurate, polyoxyethylene alkylphenyl ether sulfuric acid ester salts, polyoxyethylene alkyl ether sulfonic acid salts, phosphoric acid esters of polyoxyethylene alkyl ethers, and phosphoric acid esters of polyoxyethylene alkyl allyl ethers. Among them, the surfactant preferably includes at least one compound selected from the group consisting of sorbitan fatty acid esters, polyglycerin fatty acid esters, and sucrose fatty acid esters, from the viewpoints that then, a state of a W/O type reverse-phase suspension becomes favorable, water-absorbent resin particles are likely to be obtained with suitable particle sizes, and industrial availability becomes high. Furthermore, the surfactant more preferably includes sucrose fatty acid esters from the viewpoint that water absorption characteristics of the obtained water-absorbent resin particles are then improved. These surfactants may be used alone or in combination of two or more kinds thereof.

An amount of the surfactant is preferably 0.05 to 10 parts by mass, is more preferably 0.08 to 5 parts by mass, and is even more preferably 0.1 to 3 parts by mass, with respect to 100 parts by mass of the aqueous solution of the ethylenically unsaturated monomers, from the viewpoint that a sufficient effect is obtained within these usage amounts, and these amounts are economic.

Furthermore, a polymeric dispersant may be used in combination with the above-mentioned surfactant. Examples of polymeric dispersants include maleic anhydride-modified polyethylene, maleic anhydride-modified polypropylene, a maleic anhydride-modified ethylene-propylene copolymer, a maleic anhydride-modified EPDM (ethylene propylene diene terpolymer), maleic anhydride-modified polybutadiene, a maleic anhydride-ethylene copolymer, a maleic anhydride-propylene copolymer, a maleic anhydride-ethylene-propylene copolymer, a maleic anhydride-butadiene copolymer, polyethylene, polypropylene, an ethylene-propylene copolymer, oxidized polyethylene, oxidized polypropylene, an oxidized ethylene-propylene copolymer, an ethylene-acrylic acid copolymer, ethyl cellulose, ethyl hydroxyethyl cellulose, and the like. Among these polymeric dispersants, particularly from the viewpoint of dispersion stability of monomers, it is preferable to use maleic anhydride-modified polyethylene, maleic anhydride-modified polypropylene, a maleic anhydride-modified ethylene-propylene copolymer, a maleic anhydride-ethylene copolymer, a maleic anhydride-propylene copolymer, a maleic anhydride-ethylene-propylene copolymer, polyethylene, polypropylene, an ethylene-propylene copolymer, oxidized polyethylene, oxidized polypropylene, and an oxidized ethylene-propylene copolymer. These polymeric dispersants may be used alone or in combination of two or more kinds thereof.

An amount of the polymeric dispersant is preferably 0.05 to 10 parts by mass, is more preferably 0.08 to 5 parts by mass, and is even more preferably 0.1 to 3 parts by mass, with respect to 100 parts by mass of the aqueous solution of the ethylenically unsaturated monomers, from the viewpoint that a sufficient effect is obtained within these usage amounts, and these amounts are economic.

A radical polymerization initiator is preferably water-soluble. Examples thereof include persulfates such as potassium persulfate, ammonium persulfate, and sodium persulfate; peroxides such as methyl ethyl ketone peroxide, methyl isobutyl ketone peroxide, di-t-butyl peroxide, t-butyl cumyl peroxide, t-butyl peroxyacetate, t-butyl peroxyisobutyrate, t-butyl peroxypivalate, and hydrogen peroxide; and azo compounds such as 2,2'-azobis(2-amidinopropane) dihydrochloride, 2,2'-azobis[2-(N-phenylamidino)propane] dihydrochloride, 2,2'-azobis[2-(N-allylamidino)propane] dihydrochloride, 2,2'-azobis[2-(2-imidazolin-2-yl)propane] dihydrochloride, 2,2'-azobis{2-[1-(2-hydroxyethyl)-2-imidazolin-2-yl]propane}dihydrochloride, 2,2'-azobis{2-methyl-N-[1,1-bis(hydroxymethyl)-2-hydroxyethyl]propionamide}, 2,2'-azobis[2-methyl-N-(2-hydroxyethyl)-propionamide], and 4,4'-azobis(4-cyanovaleric acid). Among them, potassium persulfate, ammonium persulfate, sodium persulfate, 2,2'-azobis(2-amidinopropane) dihydrochloride, 2,2'-azobis[2-(2-imidazolin-2-yl)propane] dihydrochloride, and 2,2'-azobis{2-[1-(2-hydroxyethyl)-2-imidazolin-2-yl]propane}dihydrochloride are preferred. These radical polymerization initiators may be used alone or in combination of two or more kinds thereof.

A usage amount of the radical polymerization initiator may be 0.00005 to 0.01 moles with respect to 1 mole of the ethylenically unsaturated monomers. A case in which a usage amount of the radical polymerization initiator is 0.00005 moles or more is efficient, because then a polymerization reaction is not required to be performed for a long period of time. In a case where a usage amount thereof is 0.01 moles or less, a rapid polymerization reaction is unlikely to occur.

The radical polymerization initiator can also be used as a redox polymerization initiator when it is used in combination with a reducing agent such as sodium sulfite, sodium hydrogen sulfite, ferrous sulfate, and L-ascorbic acid.

In a polymerization reaction, a chain transfer agent may be contained in an aqueous solution of the ethylenically unsaturated monomers used for the polymerization. Examples of chain transfer agents include hypophosphites, thiols, thiolic acids, secondary alcohols, and amines.

Furthermore, a thickener may be contained in the aqueous solution of the ethylenically unsaturated monomers used for the polymerization to control a particle size of the water-absorbent resin particles.

As the thickener, it is possible to use, for example, hydroxyethyl cellulose, hydroxypropyl cellulose, methyl cellulose, carboxymethyl cellulose, polyacrylic acid, polyethylene glycol, polyacrylamide, polyethyleneimine, dextrin, sodium alginate, polyvinyl alcohol, polyvinylpyrrolidone, polyethylene oxide, and the like. In a case where stirring speeds in the polymerization are the same, a median particle size of particles to be obtained is likely to become large as a viscosity of the aqueous solution of the ethylenically unsaturated monomers becomes high.

The hydrocarbon dispersion medium may include at least one compound selected from the group consisting of a chained aliphatic hydrocarbon having 6 to 8 carbon atoms and an alicyclic hydrocarbon having 6 to 8 carbon atoms. Examples of hydrocarbon dispersion media include chained aliphatic hydrocarbons such as n-hexane, n-heptane, 2-methylhexane, 3-methylhexane, 2,3-dimethylpentane, 3-ethylpentane, and n-octane; alicyclic hydrocarbons such as cyclohexane, methylcyclohexane, cyclopentane, methylcyclopentane, trans-1,2-dimethylcyclopentane, cis-1,3-dimethylcyclopentane, and trans-1,3-dimethylcyclopentane; and aromatic hydrocarbons such as benzene, toluene, and xylene. These hydrocarbon dispersion media may be used alone or in combination of two or more kinds thereof. For the hydrocarbon dispersion medium, n-heptane, cyclohexane, or both n-heptane and cyclohexane may be contained, from the viewpoints of high industrial availability and stable qualities. Furthermore, from the same viewpoints, as a mixture of the hydrocarbon dispersion media, for example, a commercially available Exxsol Heptane (manufactured by ExxonMobil Chemical: containing n-heptane and 75% to 85% of hydrocarbons of isomers thereof) may be used.

A usage amount of the hydrocarbon dispersion medium is preferably 30 to 1,000 parts by mass, is more preferably 40 to 500 parts by mass, and is even more preferably 50 to 300 parts by mass, with respect to 100 parts by mass of the aqueous solution of monomers, from the viewpoint that polymerization heat is then appropriately removed, and thereby a polymerization temperature is easily controlled. In a case where a usage amount of the hydrocarbon dispersion medium is 30 parts by mass or more, there is a tendency that it becomes easy to control a polymerization temperature. In a case where a usage amount of the hydrocarbon dispersion medium is 1,000 parts by mass or less, there is a tendency that productivity of polymerization is improved, which is economic.

In general, internal crosslinking may occur by self-crosslinking upon the polymerization, but internal crosslinking may be carried out by further using an internal crosslinking agent, and thereby water absorption characteristics of the water-absorbent resin particles may be controlled. Examples of internal crosslinking agents to be used include di- or tri(meth)acrylic acid esters of polyols such as ethylene glycol, propylene glycol, trimethylolpropane, glycerin, polyoxyethylene glycol, polyoxypropylene glycol, and polyglycerin; unsaturated polyesters obtained by reacting the above mentioned polyols with unsaturated acids such as maleic acid and fumaric acid; bis(meth)acrylamides such as N,N'-methylenebis(meth)acrylamide; di- or tri(meth)acrylic acid esters obtained by reacting a polyepoxide with (meth)acrylic acid; carbamyl di(meth)acrylate esters obtained by reacting a polyisocyanate such as tolylene diisocyanate and hexamethylene diisocyanate with hydroxyethyl (meth)acrylate; compounds having two or more polymerizable unsaturated groups, such as allylated starch, allylated cellulose, diallyl phthalate, N, N', N"-triallyl isocyanurate, and divinylbenzene; polyglycidyl compounds such as (poly)ethylene glycol diglycidyl ether, (poly)propylene glycol diglycidyl ether, (poly)glycerin diglycidyl ether, (poly)glycerin diglycidyl ether, (poly)propylene glycol polyglycidyl ether, and polyglycerol polyglycidyl ether; haloepoxy compounds such as epichlorohydrin, epibromohydrin, and α-methyl epichlorohydrin; and compounds having two or more reactive functional groups, such as isocyanate compounds including, for example, 2,4-tolylene diisocyanate and hexamethylene diisocyanate. Among these internal crosslinking agents, it is preferable to use a polyglycidyl compound, it is more preferable to use a diglycidyl ether compound, and it is particularly preferable to use (poly)ethylene glycol diglycidyl ether, (poly)propylene glycol diglycidyl ether, and (poly)glycerin diglycidyl ether. These crosslinking agents may be used alone or in combination of two or more kinds thereof.

An amount of the internal crosslinking agent is preferably 0 to 0.03 moles, is more preferably 0.00001 to 0.01 moles, and is even more preferably 0.00002 to 0.005 moles, per 1 mole of the ethylenically unsaturated monomer, from the viewpoints of inhibiting water-soluble properties by appropriately crosslinking the obtained polymer, and exhibiting a sufficient water absorption capacity.

An aqueous phase containing components such as an ethylenically unsaturated monomer, a radical polymerization initiator, and if necessary, an internal crosslinking agent; and an oil phase containing components such as a hydrocarbon dispersion medium, a surfactant, and if necessary, and a polymeric dispersant can be mixed and heated under stirring to carry out reverse-phase suspension polymerization in a water-in-oil system.

When performing the reverse-phase suspension polymerization, an aqueous solution of monomers which contains ethylenically unsaturated monomers is dispersed in a hydrocarbon dispersion medium in the presence of a surfactant and if necessary, a polymeric dispersant. In this case, a timing of adding the surfactant or the polymeric dispersant before the start of the polymerization reaction may be either before or after the addition of the aqueous solution of monomers.

Among them, it is preferable to carry out the polymerization after dispersing the aqueous solution of monomers in the hydrocarbon dispersion medium in which the polymeric dispersant has been dispersed, and then further dispersing the surfactant in the hydrocarbon dispersion medium, from the viewpoint that an amount of the hydrocarbon dispersion medium remaining in the obtained water-absorbent resin can then be easily reduced.

Such reverse-phase suspension polymerization can be carried out in one stage or in multiple stages of two or more stages. Furthermore, it is preferably carried out in two or three stages from the viewpoint of increasing productivity.

In a case where reverse-phase suspension polymerization is carried out in multiple stages of two or more stages, it is sufficient for stages after a second stage of reverse-phase suspension polymerization to be carried out in the same manner as in a first stage of reverse-phase suspension polymerization by adding ethylenically unsaturated monomers to a reaction mixture obtained in the first stage of polymerization reaction and mixing them, after performing the first stage of reverse-phase suspension polymerization. In reverse-phase suspension polymerization in each stage after the second stage, it is preferable to carry out reverse-phase suspension polymerization by adding, in addition to ethylenically unsaturated monomers, the above-mentioned radical polymerization initiator and internal crosslinking agent within the above-mentioned range of molar ratios of the respective components to the ethylenically unsaturated monomers, based on an amount of ethylenically unsaturated monomers added during reverse-phase suspension polymerization in each stage after the second stage. If necessary, the internal crosslinking agent may be used in reverse-phase suspension polymerization in each stage after the second stage. In a case where the internal crosslinking agent is used, it is preferable to carry out reverse-phase suspension polymerization by adding the internal crosslinking agent within the above-mentioned range of molar ratios of the respective components to the ethylenically unsaturated monomers based on an amount of ethylenically unsaturated monomers provided in each stage.

A temperature for the polymerization reaction varies depending on radical polymerization initiators used, but it is preferably 20° C. to 150° C., and is more preferably 40° C. to 120° C., from the viewpoint that the polymerization is then promptly performed, which shortens a polymerization time, and thereby economic efficiency increases, and that polymerization heat is then easily removed, and thereby the reaction is smoothly performed. A reaction time is generally 0.5 to 4 hours. Completion of the polymerization reaction can be confirmed from, for example, stop of temperature rising in the reaction system. Accordingly, a polymer of ethylenically unsaturated monomers is generally obtained in a state of a hydrous gel.

After the polymerization, post-polymerization crosslinking may be carried out by adding a crosslinking agent to the obtained hydrous gel polymer and heating them. By performing the post-polymerization crosslinking, a degree of crosslinking of the hydrous gel polymer can be increased, and thereby water absorption characteristics can be more preferably improved.

Examples of crosslinking agents for performing the post-polymerization crosslinking include polyols such as ethylene glycol, propylene glycol, 1,4-butanediol, trimethylolpropane, glycerin, polyoxyethylene glycol, polyoxypropylene glycol, and polyglycerin; compounds having two or more epoxy groups, such as (poly)ethylene glycol diglycidyl ether, (poly)propylene glycol diglycidyl ether, and (poly)glycerin diglycidyl ether; haloepoxy compounds such as epichlorohydrin, epibromohydrin, and α-methyl epichlorohydrin; compounds having two or more isocyanate groups such as 2,4-tolylene diisocyanate and hexamethylene diisocyanate; oxazoline compounds such as 1,2-ethylenebisoxazoline; carbonate compounds such as ethylene carbonate; and hydroxyalkylamide compounds such as bis[N,N-di(β-hydroxyethyl)]adipamide. Among them, polyglycidyl compounds such as (poly)ethylene glycol diglycidyl ether, (poly)glycerin diglycidyl ether, (poly)glycerin triglycidyl ether, (poly)propylene glycol polyglycidyl ether, and polyglycerol polyglycidyl ether are preferable. These crosslinking agents may be used alone or in combination of two or more kinds thereof.

An amount of the crosslinking agent used for the post-polymerization crosslinking is preferably 0 to 0.03 moles, is more preferably 0 to 0.01 moles, and is even more preferably 0.00001 to 0.005 moles, per 1 mole of the ethylenically unsaturated monomer, from the viewpoint of exhibiting suitable water absorption characteristics by appropriately crosslinking the obtained hydrous gel polymer. In a case where an amount of the crosslinking agent added is within the above range, it is possible to easily obtain water-absorbent resin particles having a suitable liquid permeability.

It is sufficient for a timing for adding the post-polymerization crosslinking to be after polymerization of ethylenically unsaturated monomers used for the polymerization. In a case of multi-stage polymerization, the crosslinking agent is preferably added after the multi-stage polymerization. From the viewpoint of a water content (to be described later), it is preferable to add the crosslinking agent for the post-polymerization crosslinking within a region of [water content immediately after polymerization ±3% by mass], in consideration of heat generation during and after polymerization, retention due to process delay, system opening when a crosslinking agent is added, and fluctuation in moisture content due to addition of water associated with addition of a crosslinking agent.

Subsequently, drying is performed to remove moisture from the obtained hydrous gel polymer. By drying, polymer particles containing the polymer of ethylenically unsaturated monomers are obtained. Examples of drying methods include a method (a) in which the hydrous gel polymer in a state of being dispersed in a hydrocarbon dispersion medium is subjected to azeotropic distillation by heating from the outside, and the hydrocarbon dispersion medium is refluxed to remove moisture; a method (b) in which the hydrous gel polymer is taken out by decantation and dried under reduced pressure; and a method (c) in which the hydrous gel polymer is separated by filtration with a filter and dried under reduced pressure. Among them, the method (a) is preferably used for its simplicity in a production process.

Control over a particle size of the water-absorbent resin particle can be performed, for example, by adjusting a rotational speed of a stirrer during the polymerization reaction or by adding a powdery inorganic flocculating agent to the system after the polymerization reaction or at an initial time of drying. A particle size of the obtained water-absorbent resin particle can be increased by adding the flocculating agent. Examples of powdery inorganic flocculating agents include silica, zeolite, bentonite, aluminum oxide, talc, titanium dioxide, kaolin, clay, and hydrotalcite. Among them, silica, aluminum oxide, talc, or kaolin is preferable from the viewpoint of a flocculation effect.

In the reverse-phase suspension polymerization, the following method is preferable as a method of adding the powdery inorganic flocculating agent: a method in which a powdery inorganic flocculating agent is dispersed in a hydrocarbon dispersion medium of the same kind as that used in the polymerization, or water in advance, and then the mixture is mixed into a hydrocarbon dispersion medium containing a hydrous gel under stirring.

In the production of the water-absorbent resin particles according to the present embodiment, a surface portion of the hydrous gel polymer is preferably crosslinked (surface-crosslinked) using a crosslinking agent in the drying process or any of subsequent processes. The surface crosslinking is preferably performed at a timing when the hydrous gel polymer has a specific water content. A timing of the surface crosslinking is preferably a time point at which a water content of the hydrous gel polymer is 5% to 50% by mass, is more preferably a time point at which a water content thereof is 10% to 40% by mass, and is even more preferably a time point at which a water content thereof is 15% to 35% by mass.

A water content (% by mass) of the hydrous gel polymer is calculated by the following formula.

$$\text{Water content} = [Ww/(Ww + Ws)] \times 100$$

Ww: An amount of water of a hydrous gel polymer obtained by adding an amount of water used, as desired, upon mixing a powdery inorganic flocculating agent, a surface crosslinking agent, and the like to an amount obtained by subtracting an amount of water extracted to the outside of the system by the drying process from an amount of water contained in an aqueous liquid before polymerization in the all polymerization processes.

Ws: A solid fraction calculated from an amount of materials introduced, such as ethylenically unsaturated monomers, a crosslinking agent, and an initiator, each of which constitutes the hydrous gel polymer.

Examples of surface crosslinking agents for performing surface crosslinking include compounds having two or more reactive functional groups. Examples thereof include polyols such as ethylene glycol, propylene glycol, 1,4-butanediol, trimethylolpropane, glycerin, polyoxyethylene glycol, polyoxypropylene glycol, and polyglycerin; polyglycidyl compounds such as (poly)ethylene glycol diglycidyl ether, (poly)glycerin diglycidyl ether, (poly)glycerin triglycidyl ether, trimethylolpropane triglycidyl ether, (poly)propylene glycol polyglycidyl ether, and (poly)glycerol polyglycidyl ether; haloepoxy compounds such as epichlorohydrin, epibromohydrin, and α-methyl epichlorohydrin; isocyanate compounds such as 2,4-tolylene diisocyanate and hexamethylene diisocyanate; oxetane compounds such as 3-methyl-3-oxetane methanol, 3-ethyl-3-oxetane methanol, 3-butyl-3-oxetane methanol, 3-methyl-3-oxetane ethanol, 3-ethyl-3-oxetane ethanol, and 3-butyl-3-oxetane ethanol; oxazoline compounds such as 1,2-ethylenebisoxazoline; carbonate compounds such as ethylene carbonate; and hydroxyalkylamide compounds such as bis[N,N-di(β-hydroxyethyl)]adipamide. Among them, polyglycidyl compounds such as (poly)ethylene glycol diglycidyl ether, (poly)glycerin diglycidyl ether, (poly)glycerin triglycidyl ether, (poly)propylene glycol polyglycidyl ether, and polyglycerol polyglycidyl ether are more preferable. These surface crosslinking agents may be used alone or in combination of two or more kinds thereof.

In general, an amount of the surface crosslinking agent is preferably 0.00001 to 0.02 moles, is more preferably 0,00005 to 0.01 moles, and is even more preferably 0.0001 to 0.005 moles in a molar ratio, with respect to 1 mole of the ethylenically unsaturated monomer used in the polymerization, from the viewpoint of exhibiting suitable water absorption characteristics by appropriately crosslinking the obtained hydrous gel polymer.

A usage amount of the surface crosslinking agent is preferably 0.00001 moles or more from the viewpoint of sufficiently increasing a crosslinking density in a surface portion of the polymer particles and thereby enhancing gel strength of the water-absorbent resin particles. Furthermore, a usage amount thereof is preferably 0.02 moles or less from the viewpoint of increasing a water absorption capacity for a physiological saline solution under a load and increasing a water retention capacity of the water-absorbent resin particles.

It is possible to obtain polymer particles, which are a surface-crosslinked dried product, by distilling off water and the hydrocarbon dispersion medium by a known method after the surface crosslinking reaction.

A ratio of an amount of an external crosslinking agent to an amount of the internal crosslinking agent (hereinafter, also referred to as a "crosslinking proportion") of the polymer particles is preferably 6 or more, is preferably 8 or more, and is more preferably 10 or more, from the viewpoint of improving liquid permeability and setting a contact angle within a suitable range. A crosslinking proportion may be, for example, 100 or less, 80 or less, 60 or less, 40 or less, 30 or less, 20 or less, or 15 or less. An amount of the internal crosslinking agent is a total amount (mmol) of internal crosslinking agents added once or multiple times. An amount of the external crosslinking agent is a total amount (mmol) of an amount of a post-polymerization crosslinking agent and an amount of a surface crosslinking agent.

The water-absorbent resin particles according to the present embodiment may be composed of only the polymer particles, but they can further contain, for example, various additional components selected from inorganic powders, surfactants, oxidizers, reducing agents, metal chelating agents (ethylenediaminetetraacetic acid and its salts, diethylenetriaminepentaacetic acid and its salts, for example, diethylenetriaminepentaacetic acid pentasodiumn, and the like), radical chain inhibitors, antioxidants, antibacterial agents, deodorants, gel stabilizers, flowablility improvers (lubricants), and the like. The additional components may be disposed inside the polymer particles, on a surface of the polymer particles, or both of the inside and on the surface thereof. As the additional component, flowablility improvers (lubricants) are preferable, and among them, inorganic particles are more preferable. Examples of inorganic particles include silica particles such as amorphous silica. For example, flowablility of the water-absorbent resin particles can be improved by adding 0.05 to 5 parts by mass of amorphous silica as inorganic particles with respect to 100 parts by mass of the polymer particles. It is preferable that the water-absorbent resin particles according to the present embodiment do not contain non-porous spherical silicon oxide. Furthermore, the water-absorbent resin particles according to the present embodiment may not contain a cationic polymer compound containing a primary amino group and/or a secondary amino group, and/or water-soluble polyvalent metal salt particles.

The water-absorbent resin particles may contain a plurality of inorganic particles disposed on the surface of the polymer particles. The inorganic particles can be disposed on the surface of the polymer particles by, for example, mixing the polymer particles and the inorganic particles. These inorganic particles may be silica particles such as amorphous silica. In a case where the water-absorbent resin particles contain inorganic particles disposed on the surface of the polymer particles, a ratio of the inorganic particles to a mass of the polymer particles may be 0.2% by mass or more, 0.5% by mass or more, 1.0% by mass or more, or 1.5% by mass or more, and it may be 5.0% by mass or less or 3.5% by mass or less. The inorganic particles referred to herein generally have a minute size as compared with a size of the polymer particles. For example, an average particle size of the inorganic particles may be 0.1 to 50 μm, 0.5 to 30 μm, or 1 to 20 μm. The average particle size referred to herein can be a value measured by a dynamic light scattering method or a laser diffraction/scattering method. In a case where an amount of the inorganic particles added is within the above range, it is easy to obtain water-absorbent resin particles having favorable water absorption characteristics.

The water-absorbent resin particles according to the present embodiment have excellent absorbency for body fluids such as urine and blood, and they can be applied to, for example, the fields of sanitary products such as paper diapers, sanitary napkins, and tampons, and animal excrement treatment materials such as pet sheets, and dog or cat litters.

The water-absorbent resin particles according to the present embodiment can be suitably used for an absorbent. The absorbent according to the present embodiment includes the above-mentioned water-absorbent resin particles. The absorbent may further include, for example, a fibrous material.

A mass proportion of the water-absorbent resin particles in the absorbent may be 2% by mass to 100% by mass, is preferably 10% by mass to 80% by mass, and is more preferably 20% by mass to 70% by mass, with respect to a total of the water-absorbent resin particles and the fibrous material. The configuration of the absorbent may be, for example, a form in which water-absorbent resin particles and the fibrous materials are uniformly mixed, a form in which water-absorbent resin particles are held between fibrous materials formed in a sheet shape or a layer shape, or another form.

A content of the water-absorbent resin particles in the absorbent is preferably 100 to 1,000 g, is more preferably 150 to 800 g, and is even more preferably 200 to 700 g, per 1 m$^2$ of the absorbent from the viewpoint of easily obtaining a sufficient water absorption performance. A content of the fibrous material in the absorbent is preferably 50 to 800 g, is more preferably 100 to 600 g, and is even more preferably 150 to 500 g, per 1 m$^2$ of the absorbent from the viewpoint of easily obtaining a sufficient water absorption performance.

Examples of fibrous materials include finely pulverized wood pulp; cotton; cotton linter; rayon; cellulose-based fibers such as cellulose acetate; and synthetic fibers such as polyamides, polyesters, and polyolefins. The fibrous material may be a mixture of the above-mentioned fibers.

Fibers may be adhered to each other by adding an adhesive binder to the fibrous material in order to enhance shape retention properties before or during use of the absorbent. Examples of adhesive binders include thermal bonding synthetic fibers, hot-melt adhesives, and adhesive emulsions.

Examples of thermal bonding synthetic fibers include full-melt binders such as polyethylene, polypropylene, and an ethylene-propylene copolymer; and partial-melt binders formed of polypropylene and polyethylene in a side-by-side or core-and-sheath configuration. In the above-mentioned partial-melt binders, only a polyethylene portion is thermal-bonded. Examples of hot-melt adhesives include a blend of a base polymer such as an ethylene-vinyl acetate copolymer, a styrene-isoprene-styrene block copolymer, a styrene-butadiene-styrene block copolymer, a styrene-ethylene-butylene-styrene block copolymer, a styrene-ethylene-propylene-styrene block copolymer, and an amorphous polypropylene with a viscosity imparting agent, a plasticizer, an antioxidant, or the like.

Examples of adhesive emulsions include polymers of at least one or more monomers selected from the group consisting of methyl methacrylate, styrene, acrylonitrile, 2-ethylhexyl acrylate, butyl acrylate, butadiene, ethylene, and vinyl acetate. These adhesive binders may be used alone or in combination of two or more kinds thereof.

The absorbent according to the present embodiment may further contain an inorganic powder (for example, amorphous silica), a deodorant, an antibacterial agent, a fragrance, and the like. In a case where the water-absorbent resin particles contain inorganic particles, the absorbent may contain an inorganic powder in addition to the inorganic particles in the water-absorbent resin particles.

A shape of the absorbent according to the present embodiment is not particularly limited, but it may be, for example, a sheet shape. A thickness of the absorbent (for example, a thickness of a sheet-shaped absorbent) may be, for example, 0.1 to 20 mm or 0.3 to 15 mm.

The absorbent can be suitably used for an absorbent article. An absorbent article according to the present embodiment includes the absorbent according to the present embodiment. Examples of the absorbent article according to the present embodiment include a core wrap that retains the shape of the absorbent; a liquid-permeable sheet disposed on the outermost part on a side from which an absorption target liquid is infiltrated; a liquid-impermeable sheet disposed on the outermost part on a side opposite to the side from which the absorption target liquid is infiltrated; and the like. Examples of the absorbent article include diapers (for example, paper diapers), toilet training pants, incontinence pads, sanitary products (sanitary napkins, tampons, and the like), sweat pads, pet sheets, portable toilet members, animal excrement treatment materials, and the like.

Figure 1:
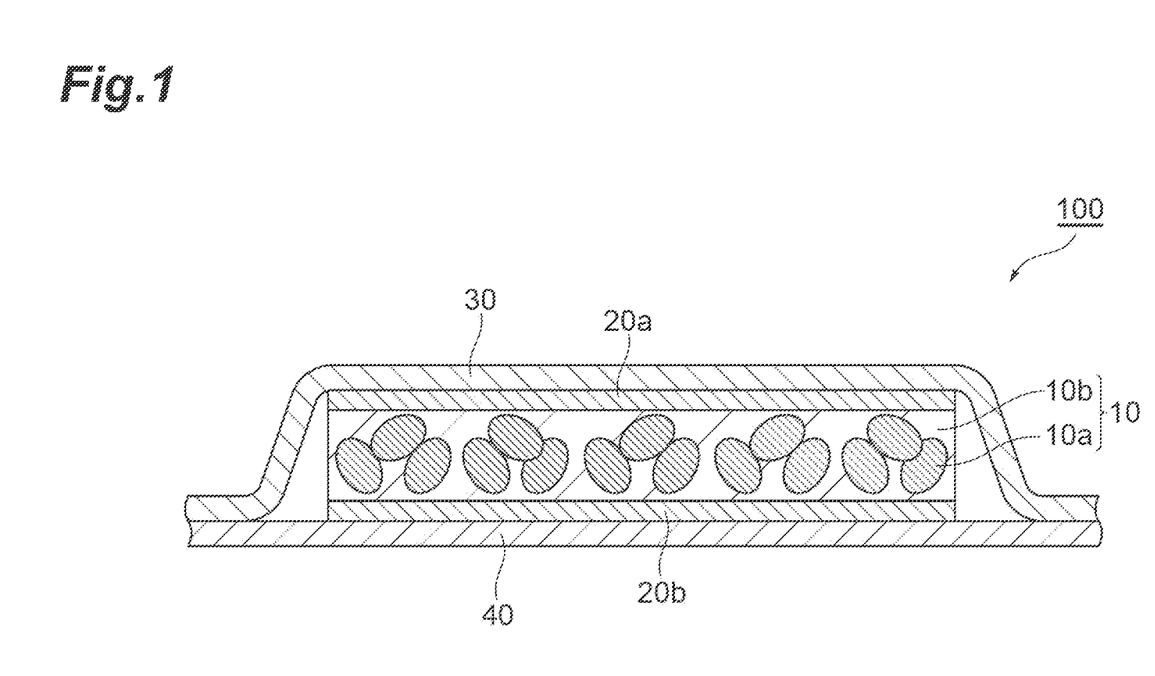
FIG. 1 is a cross-sectional view showing an example of an absorbent article.

FIG. 1 is a cross-sectional view showing an example of an absorbent article. An absorbent article 100 shown in FIG. 1 includes an absorbent 10, core wraps 20a and 20b, a liquid-permeable sheet 30, and a liquid-impermeable sheet 40. In the absorbent article 100, the liquid-impermeable sheet 40, the core wrap 20b, the absorbent 10, the core wrap 20a, and the liquid-permeable sheet 30 are laminated in this order. In FIG. 1, there is a portion shown to be a gap between the members, but the members may be in close contact with each other without the gap.

The absorbent 10 has water-absorbent resin particles 10a according to the present embodiment and a fiber layer 10b containing a fibrous material. The water absorbent resin particles 10a are dispersed in the fiber layer 10b.

The core wrap 20a is disposed on one surface side of the absorbent 10 (an upper side of the absorbent 10 in FIG. 1) in a state of being in contact with the absorbent 10. The core wrap 20b is disposed on the other surface side of the absorbent 10 (a lower side of the absorbent 10 in FIG. 1) in a state of being in contact with the absorbent 10. The absorbent 10 is disposed between the core wrap 20a and the core wrap 20b. Examples of the core wraps 20a and 20b include tissues, non-woven fabrics, and the like. The core wrap 20a and the core wrap 20b each have, for example, a main surface having the same size as that of the absorbent 10.

The liquid-permeable sheet 30 is disposed on the outermost part on a side from which an absorption target liquid is infiltrated. The liquid-permeable sheet 30 is disposed on the core wrap 20a in a state of being in contact with the core wrap 20a. Examples of the liquid-permeable sheet 30 include non-woven fabrics made of synthetic resin such as polyethylene, polypropylene, polyester, and polyimide, and porous sheets. The liquid-impermeable sheet 40 is disposed on the outermost part on a side opposite to the liquid-permeable sheet 30, in the absorbent article 100. The liquid-impermeable sheet 40 is disposed below the core wrap 20b in a state of being in contact with the core wrap 20b. Examples of the liquid-impermeable sheet 40 include sheets made of synthetic resins such as polyethylene, polypropylene, and polyvinyl chloride, and sheets made of a composite material of these synthetic resins and a non-woven fabric. The liquid-permeable sheet 30 and the liquid-impermeable sheet 40 each have, for example, a main surface wider than the main surface of the absorbent 10, and outer edges of the liquid-permeable sheet 30 and the liquid-impermeable sheet 40 respectively extend around the absorbent 10 and the core wraps 20a and 20b.

A magnitude relationship between the absorbent 10, the core wraps 20a and 20b, the liquid-permeable sheet 30, and the liquid-impermeable sheet 40 is not particularly limited, and it is appropriately adjusted according to usage applications and the like of the absorbent article. Furthermore, a method of retaining the shape of the absorbent 10 using the core wraps 20a and 20b is not particularly limited. The absorbent may be wrapped with a plurality of the core wraps as shown in FIG. 1, or the absorbent may be wrapped with one core wrap.

EXAMPLES

Hereinafter, the present invention will be described in more detail with reference to examples, but the present invention is not limited to these examples.

Production of Water-Absorbent Resin Particles

Example 1

A cylindrical round-bottomed separable flask was prepared, which had an inner diameter of 11 cm and a capacity of 2 L, and was equipped with a reflux condenser, a dropping funnel, a nitrogen gas introduction tube, and as a stirrer, a stirring blade having four inclined paddle blades, each having a blade diameter of 5 cm, in a two-tier manner. 293 g of n-heptane as a hydrocarbon dispersion medium was weighed into this flask, and 0.736 g of a maleic anhydride-modified ethylene-propylene copolymer (HI-WAX 1105A, manufactured by Mitsui Chemicals, Inc.) as a polymeric dispersant was added thereinto. The reaction solution in the flask was heated to 80° C. while being stirred to dissolve the polymeric dispersant. Thereafter, the reaction solution was cooled to 50° C.

Meanwhile, 92.0 g (1.03 moles) of an aqueous solution of 80.5% by mass acrylic acid as an ethylenically unsaturated monomer was weighed into a beaker with an internal capacity of 300 ml, and 147.7 g of an aqueous solution of 20.9% by mass sodium hydroxide was added dropwise thereto while cooling the beaker from the outside to perform neutralization to 75 mol %. Thereafter, 0.092 g of hydroxyethyl cellulose (HEC AW-15F, manufactured by Sumitomo Seika Chemicals Co., Ltd.) as a thickener, 0.092 g (0.339 mmol) of 2,2'-azobis(2-amidinopropane) dihydrochloride and 0.018 g (0.068 mmol) of potassium persulfate as a radical polymerization initiator, and 0.010 g (0.057 mmol) of ethylene glycol diglycidyl ether as an internal crosslinking agent were added and dissolved to prepare a first-stage aqueous liquid.

The prepared aqueous liquid was added into the reaction solution in the separable flask and stirred for 10 minutes. Then, a surfactant solution, in which 0.736 g of sucrose stearic acid ester (HLB: 3, manufactured by Mitsubishi-Chemical Foods Corporation, RYOTO Sugar Ester S-370) as a surfactant was dissolved in 6.62 g of n-heptane by heating, was further added into the reaction solution. While stirring the reaction solution at 550 rpm as a rotational speed of the stirrer, the inside of the system was sufficiently replaced with nitrogen. Thereafter, the flask was immersed in a water bath at 70° C. to raise its temperature, and polymerization was performed for 60 minutes. Thereby, a first-stage polymerization slurry liquid was obtained.

Meanwhile, 128.8 g (1.43 moles) of an aqueous solution of 80.5% by mass acrylic acid as an ethylenically unsaturated monomer was weighed into another beaker with an internal capacity of 500 ml, and 159.0 g of an aqueous solution of 27% by mass sodium hydroxide was added dropwise thereto while cooling the beaker from the outside to perform neutralization to 75 mol %. Thereafter, as a radical polymerization initiator, 0.129 g (0.475 mmol) of 2,2'-azobis(2-amidinopropane) dihydrochloride and 0.026 g (0.095 mmol) of potassium persulfate were added and dissolved to prepare a second-stage aqueous liquid.

While stirring at 1,000 rpm as a rotational speed of the stirrer, the inside of the separable flask system was cooled to 25° C. Then, a total amount of the second-stage aqueous liquid was added into the first-polymerization slurry liquid in the separable flask, and the inside of the system was replaced with nitrogen for 30 minutes. Thereafter, the flask was immersed in a water bath at 70° C. again to raise its temperature, and a polymerization reaction was performed for 60 minutes. Thereafter, 0.580 g (0.067 mmol) of an aqueous solution of 2% by mass ethylene glycol diglycidyl ether was added as a crosslinking agent for post-polymerization crosslinking, and thereby a hydrous gel polymer was obtained.

Under stirring, 0.265 g of an aqueous solution of 45% by mass diethylenetriaminepentaacetic acid pentasodium was added into the reaction solution containing the hydrous gel polymer obtained after the second-stage polymerization. Thereafter, the flask was immersed in an oil bath set to 125°

C., and 238.5 g of water was extracted out of the system while n-heptane was refluxed by azeotropic distillation with n-heptane and water. Thereafter, 4.42 g (0.507 mmol) of an aqueous solution of 2% by mass ethylene glycol diglycidyl ether as a surface crosslinking agent was added into the flask, and maintained at 83° C. for 2 hours.

Thereafter, n-heptane was evaporated at 125° C., and the residue was dried to obtain polymer particles (dried product). These polymer particles were passed through a sieve having an aperture of 850 nm, and 0.2% by mass of amorphous silica (Oriental Silicas Corporation, Tokusil NP-S) with respect to a mass of the polymer particles was mixed with the polymer particles. Thereby, 232.1 g of water-absorbent resin particles containing the amorphous silica was obtained. A median particle size of the water-absorbent resin particles was 396 μm, and a water absorption speed of the water-absorbent resin particles for a physiological saline solution was 39 seconds. A ratio of the amount of the external crosslinking agent to the amount of the internal crosslinking agent (crosslinking proportion) was 10.1. An amount of the internal crosslinking agent is a total amount (mmol) of internal crosslinking agents added once or twice. An amount of the external crosslinking agent is a total amount (mmol) of an amount of a post-polymerization crosslinking agent and an amount of a surface crosslinking agent.

Example 2

236.3 g of water-absorbent resin particles were obtained in the same manner as in Example 1 except that a blending amount of amorphous silica with respect to polymer particles (dried product) was changed to 2.0% by mass. A median particle size of the water-absorbent resin particles was 393 μm, and a water absorption speed of the water-absorbent resin particles for a physiological saline solution was 38 seconds. A crosslinking proportion was 10.1.

Example 3

231.0 g of water-absorbent resin particles was obtained in the same manner as in Example 1 except that, in preparation of a first-stage aqueous liquid, an amount of potassium persulfate as a radical polymerization initiator was changed to 0.0736 g (0.272 mmol), but 2,2'-azobis(2-amidinopropane) dihydrochloride was not used; in preparation of a second-stage aqueous liquid, an amount of potassium persulfate as a radical polymerization initiator was changed to 0.090 g (0.334 mmol), but 2,2'-azobis(2-amidinopropane) dihydrochloride was not used; in a reaction solution containing a hydrous gel polymer obtained after second-stage polymerization, an amount of water extracted out of the system by azeotropic distillation was changed to 247.9 g; and a blending amount of amorphous silica with respect to polymer particles was changed to 0.5% by mass. A median particle size of the water-absorbent resin particles was 355 μm, and a water absorption speed of the water-absorbent resin particles for a physiological saline solution was 37 seconds. A crosslinking proportion was 10.1.

Reference Example 1

229.2 g of water-absorbent resin particles was obtained in the same manner as in Example 1 except that, in preparation of a first-stage aqueous liquid, an amount of potassium persulfate as a radical polymerization initiator was changed to 0.0736 g (0.272 mmol), but 2,2'-azobis(2-amidinopropane) dihydrochloride was not used; in preparation of a second-stage aqueous liquid, an amount of potassium persulfate as a radical polymerization initiator was changed to 0.090 g (0.334 mmol), but 2,2'-azobis(2-amidinopropane) dihydrochloride was not used; in a reaction solution containing a hydrous gel polymer obtained after second-stage polymerization, an amount of water extracted out of the system by azeotropic distillation was changed to 239.7 g; and a blending amount of amorphous silica with respect to polymer particles was changed to 0.5% by mass. A median particle size of the water-absorbent resin particles was 377 μm, and a water absorption speed of the water-absorbent resin particles for a physiological saline solution was 40 seconds. A crosslinking proportion was 10.1.

Reference Example 2

229.6 g of water-absorbent resin particles was obtained in the same manner as in Example 1 except that, in preparation of a first-stage aqueous liquid, an amount of ethylene glycol diglycidyl ether as an internal crosslinking agent was changed to 0.0046 g (0.026 mmol); and in a reaction solution containing a hydrous gel polymer obtained after second-stage polymerization, an amount of water extracted out of the system by azeotropic distillation was changed to 219.2 g, and an amount of an aqueous solution of 2% by mass ethylene glycol diglycidyl ether as a surface crosslinking agent was changed to 6.62 g (0.761 mmol). A median particle size of the water-absorbent resin particles was 356 μm, and a water absorption speed of the water-absorbent resin particles for a physiological saline solution was 56 seconds. A crosslinking proportion was 31.8.

Comparative Example 1

229.6 g of water-absorbent resin particles was obtained in the same manners in Example 1 except that, in preparation of a first-stage aqueous liquid, an amount of ethylene glycol diglycidyl ether as an internal crosslinking agent was changed to 0.0046 g (0.026 mmol); in preparation of a second-stage aqueous liquid, 0.0116 g (0.067 mmol) of ethylene glycol diglycidyl ether was added as an internal crosslinking agent; a crosslinking agent for post-polymerization crosslinking was not added; and in a reaction solution containing a hydrous gel polymer obtained after second-stage polymerization, an amount of water extracted out of the system by azeotropic distillation was changed to 234.2 g. A median particle size of the water-absorbent resin particles was 355 μm, and a water absorption speed of the water-absorbent resin particles for a physiological saline solution was 48 seconds. A crosslinking proportion was 5.5.

Comparative Example 2

222.2 g of water-absorbent resin particles was obtained in the same manner as in Example 1 except that, in preparation of a first-stage aqueous liquid, an amount of ethylene glycol diglycidyl ether as an internal crosslinking agent was changed to 0.0368 g (0.211 mmol); in preparation of a second-stage aqueous liquid, an amount of ethylene glycol diglycidyl ether as an internal crosslinking agent was changed to 0.0515 g (0.296 mmol); a crosslinking agent for post-polymerization crosslinking was not added; and in a hydrous gel polymer obtained after second-stage polymerization, an amount of water extracted by azeotropic distillation was changed to 286.9 g. A median particle size of the particles was 396 μm, and a water absorption speed of the particles for a physiological saline solution was 67 seconds. A crosslinking proportion was 1.0.

Comparative Example 3

A cylindrical round-bottomed separable flask was prepared, which had an inner diameter of 11 cm and a capacity of 2 L, and was equipped with a reflux condenser, a dropping funnel, a nitrogen gas introduction tube, and as a stirrer, a stirring blade having four inclined paddle blades, each having a blade diameter of 5 cm, in a two-tier manner. 281 g of cyclohexane as a hydrocarbon dispersion medium was weighed into this flask, and 0.564 g of ethyl cellulose (manufactured by Ashland, Aqualon N100) was added thereinto. While stirring the mixture at 700 rpm as a rotational speed of the stirrer, nitrogen gas was blown into the system to expel dissolved oxygen. The flask was immersed in a water bath at 80° C. and heated to 75° C.

Meanwhile, 92.0 g (1.28 moles) of 100% by mass acrylic acid as an ethylenically unsaturated monomer was weighed into a beaker with an internal capacity of 300 ml, and 142.0 g of an aqueous solution of 27% by mass sodium hydroxide was added dropwise thereto while cooling the beaker from the outside to perform neutralization to 75 mol %. Thereafter, a solution, obtained by dissolving 0.184 g (0.681 mmol) of potassium persulfate as a radical polymerization initiator in 14.8 g of water, was added into the reaction solution and dissolved. Thereafter, nitrogen gas was blown into the system to remove oxygen remaining in the aqueous solution, and thereby an aqueous solution of monomers was prepared.

The prepared aqueous solution of monomers was added dropwise into the above separable flask system using a tube pump over 1 hour to carry out a polymerization reaction. After the polymerization, the flask was immersed in an oil bath set to 125° C. while stirring at 1,000 rpm as a rotational speed of the stirrer, and 107.2 g of water was extracted out of the system while cyclohexane was refluxed by azeotropic distillation with cyclohexane and water.

Thereafter, 0.036 g (0.176 mmol) of polyglycerol polyglycidyl ether (manufactured by Nagase Kasei Kogyo Co., Ltd., DENACOL EX-512) was added and dissolved in 3.61 g of water as a surface crosslinking agent in the flask. The reaction was carried out at 75° C. to 80° C. for 1 hour while heating the flask in an oil bath. Immediately after the reaction, the cyclohexane phase was separated by filtration through a sieve having an aperture of 38 μm, and thereby a water-absorbent resin hydrous product was obtained.

This water-absorbent resin hydrous product was dried in a vacuum drier set at 90° C. under heating and decompression of 0.006 MPa. Thereby, polymer particles were obtained. These particles were passed through a sieve having an aperture of 850 μm, and 0.5% by mass of amorphous silica (Oriental Silicas Corporation, Tokusil NP-S) with respect to a mass of the polymer particles (dried product) was mixed with the polymer particles. Thereby, 105.1 g of water-absorbent resin particles containing the amorphous silica was obtained. A median particle size of the water-absorbent resin particles was 310 μm, and a water absorption speed of the water-absorbent resin particles for a physiological saline solution was 78 seconds. A crosslinking proportion could not be calculated since the internal crosslinking agent was not used.

The obtained water-absorbent resin particles were evaluated for a contact angle, an artificial urine permeation speed when the water-absorbent resin particles were swollen tenfold, a water absorption capacity for a physiological saline solution under a load, a water retention capacity for a physiological saline solution, a median particle size, a surface drying index, and a water absorption speed by the following method.

<Measurement of Contact Angle>

A contact angle was measured in the environment of a temperature of 25° C. and a relative humidity of 60±10%. A double-sided tape (NICETACK manufactured by NICHIBAN Co., Ltd.: 10 mm×75 mm) was attached to a glass slide (25 mm×75 min) to prepare the glass slide on which an adhesive surface was exposed. First, 2.0 g of water-absorbent resin particles were uniformly dispersed on the double-sided tape attached to the slide. Thereafter, the slide was stood vertically to remove excess water-absorbent resin particles, and thereby a measurement sample was prepared.

A contact angle meter (manufactured by Kyowa Interface Science Co., Ltd.: Face s-150) is composed of a sample mounting stage that can move up and down, a syringe part installed above it, and a scope part by which the stage can be horizontally observed. A contact angle was measured by the following procedure using such a contact angle meter.

First, the measurement sample was placed on the stage part vertically below the syringe (capacity: 1 ml). A spherical liquid droplet, with a diameter of 3 mm, of a 25% by mass saline solution was prepared at a tip portion of the syringe using the scope of the contact angle meter. A diameter of the spherical liquid droplet was acceptable up to ±0.1 mm. The stage was moved upwards to bring the prepared liquid droplet into contact with a position at which a surface of the sample was smooth (where this timing is defined as t=0 (seconds)). An angle between a straight line, which connected left and right end points on the contact surface between the liquid droplet of the saline solution and the surface of the double-sided tape and an apex point of the liquid droplet, and the surface of the double-sided tape was read by a lens of the contact angle meter at a timing of t=30 (seconds), and this angle was defined as θ/2. The above angle was doubled to obtain a contact angle θ. The measurement was repeated 5 times, and an average value was defined as a contact angle of the water-absorbent resin particles. The angle reading method conforms to "Testing Method Of Wettability Of Glass Substrate Surface" in JIS R 3257 (1999). The results are shown in Table 1.

<Preparation of Artificial Urine>

A solution was prepared by blending and dissolving components in ion exchange water so that inorganic salts were present as shown below. A small amount of Blue No. 1 was further blended therein, and thereby artificial urine (test solution) was prepared. The following concentrations are concentrations based on a total mass of the artificial urine.

Composition of Artificial Urine
  NaCl: 0.780% by mass
  $CaCl_2$: 0.022% by mass
  $MgSO_4$: 0.038% by mass
  Blue No. 1: 0.002% by mass <Measurement of Artificial Urine Permeation Speed when Water-Absorbent Resin Particles were Swollen Tenfold>

(a) Installation of Measuring Device

Figure 2:
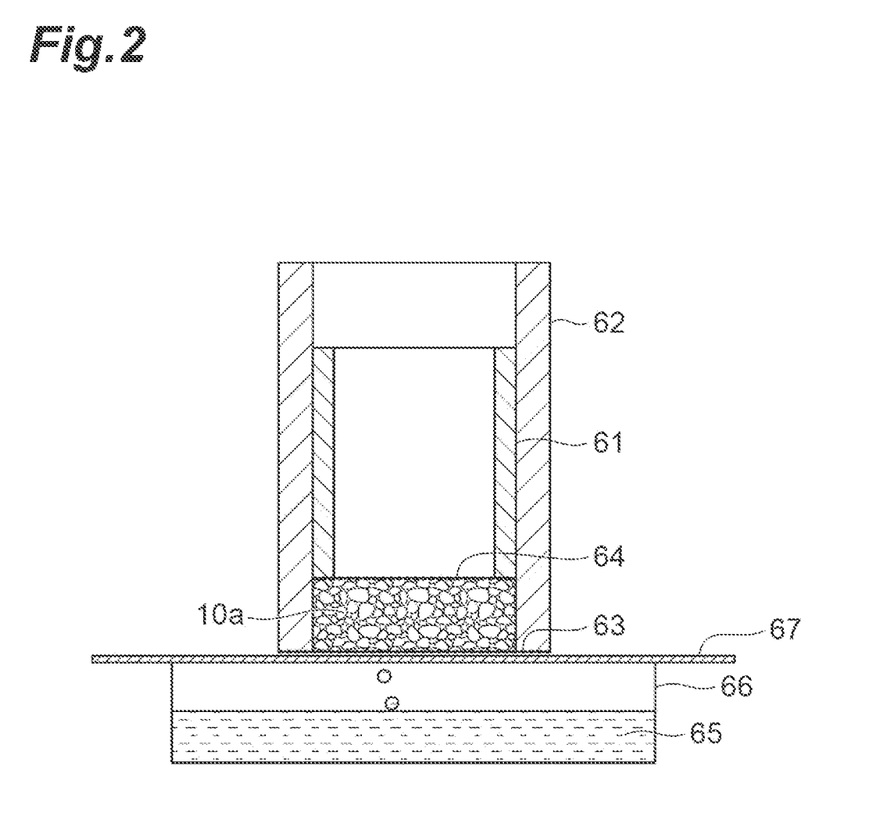
FIG. 2 is a schematic view showing a measuring device for an artificial urine permeation speed when water-absorbent resin particles are swollen tenfold.

As a measuring device, the one of which a schematic configuration is shown in FIG. 2 was used. A measuring part is composed of an acrylic resin cylindrical container (A) 61 which has an inner diameter of 19 mm, an outer diameter of 25 mm, a height of 120 mm, and a weight of about 30 g, and to which a nylon mesh sheet (250 mesh) 64 is adhered; an acrylic resin cylindrical container (B) 62 which has an inner diameter of 26 mm, an outer diameter of 40 mm, and a height of 140 mm, and to which a nylon mesh sheet 63 is adhered in the same manner; and swollen water-absorbent resin particles 10*a*. The cylindrical container (B) can move up and down inside the cylindrical container (A) without resistance. A petri dish 66 has an inner diameter of about 70 mm.

(b) Measurement of Liquid Permeation Speed

The measurement was performed at room temperature of about 25° C. 0.20 g of water-absorbent resin particles were uniformly put into the cylindrical container (B) 62, and the cylindrical container (A) 61 was inserted from above to form the measuring part. A mesh side of the measuring part was immersed in a petri dish having an inner diameter of 30 mm into which 1.8 g of artificial urine was put, and the water-absorbent resin particles were swollen for 10 minutes. Thereby, the water-absorbent resin particles were swollen tenfold.

A mass (Wa) was measured in a state where a dried wire mesh 67 having an aperture of 1.4 min (100 mm×100 mm) was placed on the empty petri dish 66. Then, the measuring part containing the swollen water-absorbent resin particles 10*a* was placed on the center of the wire mesh 67. Then, 20 g of the artificial urine was added from an upper part of the cylindrical container (A) 61, and at the same time, a stopwatch was started. 30 seconds after the addition of the artificial urine, the measuring part containing the water-absorbent resin particles 10*a* was removed from the wire mesh 67. A total mass (Wb) of the petri dish 66, which contained the artificial urine 65 that had passed through the swollen water-absorbent resin particles 10*a* and flowed out until the lapse of 30 seconds (0.5 minutes) after the addition, and the wire mesh 67 was measured. An artificial urine permeation speed (g/min) was obtained by the following formula. The results are shown in Table 1.

Artificial urine permeation speed (g/min)=(*Wb*−*Wa*)/0.5

<Measurement of Water Absorption Capacity for Physiological Saline Solution under Load of 4.14 kPa>

Figure 3:
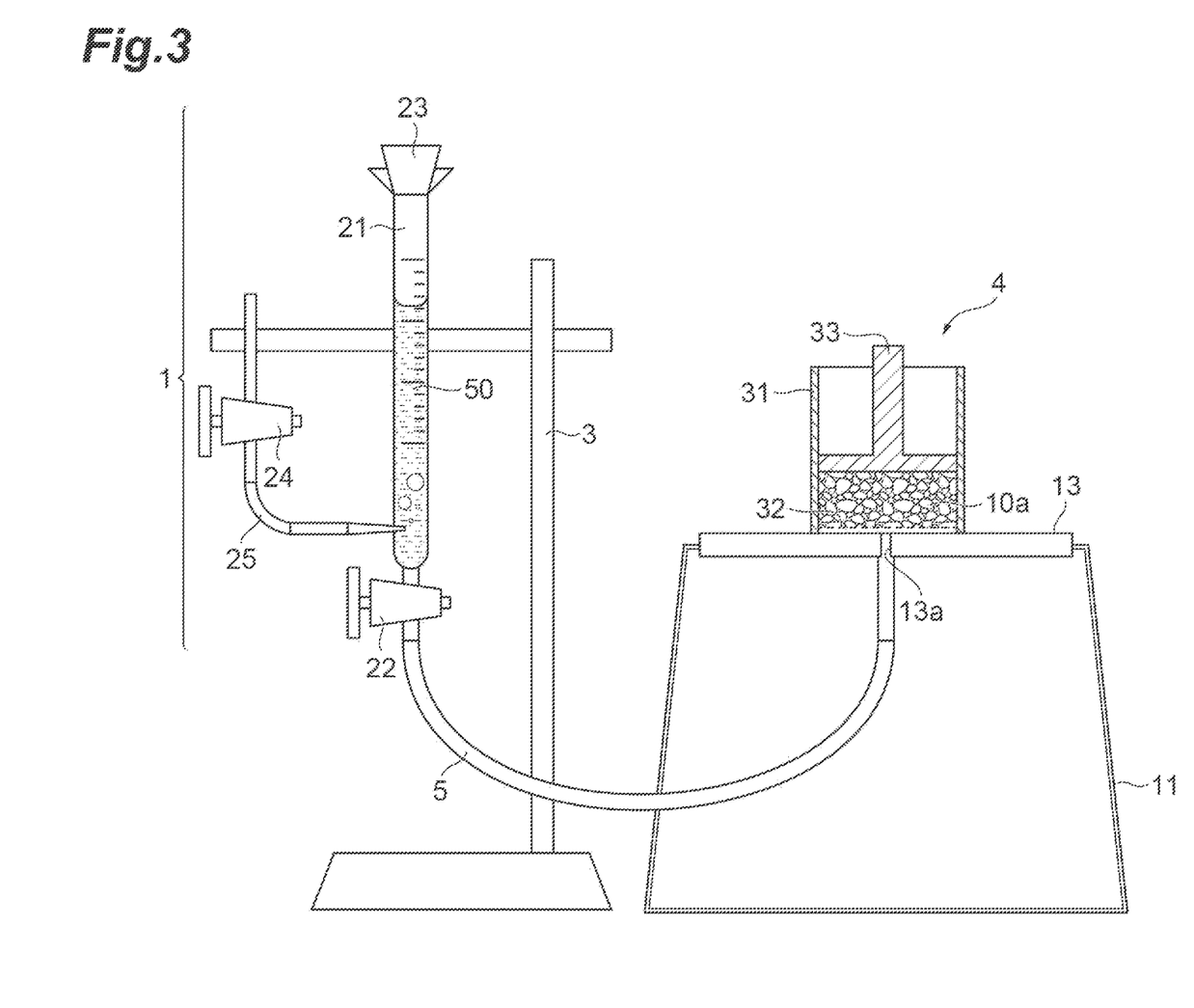
FIG. 3 is a schematic view showing a measuring device for a water absorption capacity under a load.

A water absorption capacity for a physiological saline solution under a load of 4.14 kPa (water absorption capacity under a load) was measured using a measuring device schematically shown in FIG. 3. The measurement was performed twice for one type of water-absorbent resin particles, and an average value was obtained. A measuring device includes a burette part 1, a clamp 3, a conduit pipe 5, a stand 11, a measuring stand 13, and a measuring part 4 placed on the measuring stand 13. The burette part 1 has a burette tube 21 on which a scale is engraved, a rubber stopper 23 for sealing an opening at an upper part of the burette tube 21, a cock 22 connected to a distal end of a lower part of the burette tube 21, an air introducing pipe 25 connected to the lower part of the burette tube 21, and a cock 24. The burette part 1 is fixed by the clamp 3. The flat plate-shaped measuring stand 13 has a through-hole 13*a* having a diameter of 2 mm and formed in the center portion of the measuring stand 13, and is supported by the height-variable stand 11. The through-hole 13*a* of the measuring stand 13, and the cock 22 of the burette part 1 are connected by the conduit pipe 5. An inner diameter of the conduit pipe 5 is 6 mm.

The measuring part 4 has a cylinder 31 made of plexiglass, a polyamide mesh 32 adhered to one opening of the cylinder 31, and a weight 33 that can move up and down in the cylinder 31. The cylinder 31 is placed on the measuring stand 13 with the polyamide mesh 32 therebetween. An inner diameter of the cylinder 31 is 20 mm. An aperture of the polyamide mesh 32 is 75 μm (200 mesh). The weight 33 has a diameter of 19 mm and a mass of 119.6 g, and can apply a load of 4.14 kPa (0.6 psi) to the water-absorbent resin particles 10*a* uniformly disposed on the polyamide mesh 32 as described later.

The measurement of a water absorption capacity for a physiological saline solution under a load of 4.14 kPa was performed in a room at 25° C. by using the measuring device shown in FIG. 3. First, the cock 22 and the cock 24 of the burette part 1 were closed, and a 0.9% by mass physiological saline solution that had been adjusted to 25° C. was put into the burette tube 21 through the opening at the upper part of the burette tube 21. Next, the opening on the upper part of the burette tube 21 was sealed with the rubber stopper 23, and then the cock 22 and the cock 24 were opened. The inside of the conduit pipe 5 was filled with the 0.9% by mass saline solution 50 to prevent air bubbles from entering. A height of the measuring stand 13 was adjusted so that a height of a water surface of the 0.9% by mass saline solution, which had reached the inside of the through-hole 13*a*, was the same as a height of an upper surface of the measuring stand 13. After the adjustment, the height of the water surface of the 0.9% by mass saline solution 50 in the burette tube 21 was read by the scale on the burette tube 21, and this position was defined as a zero point (value read at 0 seconds).

In the measuring part 4, 0.10 g of the water-absorbent resin particles 10*a* was uniformly disposed on the polyamide mesh 32 in the cylinder 31, the weight 33 was disposed on the water-absorbent resin particles 10*a*, and the cylinder 31 was installed such that its center coincided with a conduit pipe port at the center of the measuring stand 13. An amount of decrease Wc (ml) in the physiological saline solution in the burette tube 21 60 minutes after the water-absorbent resin particles 10*a* started absorbing the physiological saline solution through the conduit pipe 5 (that is, an amount of the physiological saline solution absorbed by the water-absorbent resin particles 10*a*) was read, and a water absorption capacity of the water-absorbent resin particles 10*a* for the physiological saline solution under a load of 4.14 kPa was calculated by the following formula. The results are shown in Table 1.

Water absorption capacity (ml/g) for physiological saline solution under load of 4.14 kPa=*Wc* (ml)/mass of water-absorbent resin particles (g)

<Measurement of Water Retention Capacity for Physiological Saline Solution>

A cotton bag (cotton broadcloth No. 60, 100 mm in width×200 mm in length) into which 2.0 g of the water-absorbent resin particles had been weighed was placed in a beaker having a capacity of 500 ml. 500 g of an aqueous solution of 0.9% by mass sodium chloride (physiological saline solution) was poured into the cotton bag containing the water-absorbent resin particles at once so that a lump could not be produced. The upper part of the cotton bag was bound with a rubber band and left to stand for 30 minutes, and thereby the water-absorbent resin particles were swollen. The cotton bag after an elapse of 30 minutes was dehydrated for 1 minute using a dehydrator (manufactured by KOKUSAN Co., Ltd., product number: H-122) which had been set at a centrifugal force of 167 G, and a mass Wd (g) of the dehydrated cotton bag containing the swollen gel was measured. By performing the same operation without addition of the water-absorbent resin particles, a mass We (g) of an empty cotton bag upon moisturizing was measured, and a water retention capacity for a physiological saline solution was calculated by the following formula. The results are shown in Table 1.

Water retention capacity for physiological saline solution (g/g)=[Wd−We]/2.0

<Measurement of Median Particle Size (Particle Size Distribution)>

50 g of the water-absorbent resin particles was used for measuring a median particle size (particle size distribution). JIS standard sieves were combined in the following order from the top: a sieve having an aperture of 850 μm, a sieve having an aperture of 500 μm, a sieve having an aperture of 425 μm, a sieve having an aperture of 300 μm, a sieve having an aperture of 250 μm, a sieve having an aperture of 180 μm, a sieve having an aperture of 150 μm, and a receiving tray.

The water-absorbent resin particles were fed to the topmost sieve among the combination of the sieves, shaken for 20 minutes using a Ro-Tap shaker, and thereby classified. After the classification, a mass of the water-absorbent resin particles remaining on each of the sieves was calculated as a mass percentage with respect to a total amount to determine a particle size distribution. By integrating values on the sieves in descending order of the particle sizes with regard to the particle size distribution, a relationship between the aperture of the sieve and the integrated value of mass percentages of the water-absorbent resin particles remaining on the sieve was plotted on a log-probability paper. The plotted points on the probability paper were connected with straight lines, and a particle size corresponding to 50% by mass of the integrated mass percentage was taken as a median particle size.

<Measurement of Water Absorption Speed for Physiological Saline Solution>

50±0.1 g of an aqueous solution of 0.9% NaCl, which had been adjusted to a temperature of 25±0.2° C. in a thermostatic water bath, was weighed into a 100 ml beaker and stirred with a magnetic stirrer bar (8 mmφ×30 mm, without a ring) to generate a vortex at a rotational speed of 600 rpm. 2.0±0.002 g of the water-absorbent resin particles was added into the aqueous solution of 0.9% NaCl at once, and a time (sec) until the vortex on the liquid surface became calm after the addition of the water-absorbent resin particles was measured. The time was taken as a water absorption speed of the water-absorbent resin particles. This water absorption speed is also expressed as a Vortex method or a vortex time.

<Corneometer Measurement>

[Production of Absorbent Article]

13.3 g of the water-absorbent resin particles and 12.9 g of pulverized pulp were uniformly mixed by air papermaking using an air flow type mixer (Padformer manufactured by O-TEC Co., Ltd.), and thereby a sheet-shaped absorbent having a size of 40 cm×12 cm was produced. Then, in a state where the absorbent was sandwiched from its upper and lower sides with two sheets of tissue paper, as core wraps, having a basis weight of 16 g/m$^2$ and having the same size as that of the absorbent, a load of 588 kPa was applied to the entire absorbent for 30 seconds to press it. Thereby, a laminate was obtained. Furthermore, an air-through type porous liquid-permeable sheet, which was made of polyethylene-polypropylene, had a basis weight of 22 g/m$^2$, and had the same size as that of the absorbent, was disposed on the upper surface of the laminate. Furthermore, a liquid-impermeable sheet, which was made of polyethylene and had the same size as that of the absorbent, was bonded to a surface on the side opposite to the air-through type porous liquid-permeable sheet, and thereby an absorbent article was produced.

[Corneometer Measurement]

Corneometer measurement is a method of measuring a moisture content on a surface of an object based on an electrostatic capacitance measurement method. In the electrostatic capacitance measurement method, a moisture content can be measured by utilizing a significant difference present between permittivity of water and permittivity of another substances. In the corneometer measurement, a moisture content is expressed with an index from 0 to 120.

160 ml of a 0.9% by mass physiological saline solution (25° C.) was prepared in a 200 ml graduated cylinder, and injected into the center of an absorbent article using a liquid injection cylinder having an opening with an inner diameter of 3 cm. A timing of the injection was defined as 0 minutes. A moisture content index after a predetermined time was measured using a Corneometer (manufactured by Courage+ Khazaka electronic GmbH, CM825). Specifically, a measurement probe (49 mm$^2$) attached to the Corneometer was pressed against the center of the absorbent article, and moisture content indexes on the surface of the absorbent article 1 minute and 1.5 minutes after the injection of the physiological saline solution were measured with a constant force (1N±10%). The measurement was performed in the environment of 25° C. 1° C. and a relative humidity of 50%±5%.

A measurement point of the absorbent article was touched with a finger in the corneometer measurement of the absorbent article. When a moisture content index exceeded 100, the finger got wet; when a moisture content index was about 50 to 60, the finger did not get wet, but moisture was slightly felt; and when a moisture content index was 10 or lower, moisture was not felt.

From the obtained measurement values, a surface drying index was calculated by the following formula. This index is an index of how quickly the surface of an absorbent article dries in 30 seconds after an injected physiological saline solution permeates the inside of the absorbent article to some extent in 1 minute, where this index is more preferable as a numerical value becomes lower. The results are shown in Table 2. It was shown that the absorbent article formed using the water-absorbent resin particles of the examples had a sufficiently low surface drying index.

Surface drying index=(moisture content index 1.5 minutes after liquid injection/moisture content index 1 minute after liquid injection×100

TABLE 1

| | Water retention capacity (g/g) | Water absorption capacity under load (ml/g) | Contact angle (°) | Artificial urine permeation speed when water-absorbent resin particles are swollen tenfold (g/min) |
|---|---|---|---|---|
| Example 1 | 41 | 20 | 61 | 3.3 |
| Example 2 | 41 | 20 | 28 | 3.0 |
| Example 3 | 35 | 23 | 33 | 1.6 |
| Reference Example 1 | 31 | 25 | 44 | 12.3 |
| Reference Example 2 | 28 | 26 | 64 | 31.0 |
| Comparative Example 1 | 51 | 18 | 92 | 0.0 |
| Comparative Example 2 | 36 | 9 | 64 | 0.0 |
| Comparative Example 3 | 30 | 14 | 76 | 9.0 |

TABLE 2

| | Corneometer measurement | | |
|---|---|---|---|
| | Value of moisture content index after 1 minute | Value of moisture content index after 1.5 minutes | Surface drying index (value after 1.5 minutes/value after 1 minute) × 100 |
| Example 1 | 45 | 10 | 22 |
| Example 2 | 60 | 24 | 40 |
| Example 3 | 23 | 8 | 35 |
| Reference Example 1 | 32 | 4 | 12 |
| Reference Example 2 | 101 | 13 | 13 |
| Comparative Example 1 | 113 | 78 | 69 |
| Comparative Example 2 | 117 | 116 | 99 |
| Comparative Example 3 | 89 | 88 | 99 |

REFERENCE SIGNS LIST

1 burette part, 3 clamp, 4 measuring part, 5 conduit pipe, 10 absorbent, 10a water-absorbent resin particle, 10b fiber layer, 11 stand, 13 measuring stand, 13a through-hole, 20a, 20b core wrap, burette tube, 22 cock, 23 rubber stopper, 24 cock, 25 air introducing pipe, 30 liquid-permeable sheet, 31 cylinder, 32 polyamide mesh, 33 weight, 40 liquid-impermeable sheet, 61 cylindrical container (A), 62 cylindrical container (B), 63, 64 nylon mesh sheet, 64 artificial urine, 66 petri dish, 67 wire mesh, 100 absorbent article

The invention claimed is:

1. Water-absorbent resin particles comprising:
a crosslinked polymer having a monomer unit derived from an ethylenically unsaturated monomer including at least one compound selected from the group consisting of (meth)acrylic acid and a salt thereof,
wherein a proportion of (meth)acrylic acid and a salt thereof is 70 to 100 mol % with respect to a total amount of monomer units in the crosslinked polymer, and
an artificial urine permeation speed when the water-absorbent resin particles are swollen tenfold is 1.0 g/min or more and 35.0 g/min or less, a water retention capacity for a physiological saline solution is 32 to 60 g/g, and a contact angle measured in a test performed in the order of i) and ii) below is 44 degrees or larger and 70 degrees or smaller, i) a spherical liquid droplet, which corresponds to a diameter of 3.0±0.1 mm, of a 25% by mass saline solution is added dropwise at 25° C. onto a surface of a layer formed from the water-absorbent resin particles to bring the water-absorbent resin particles into contact with the liquid droplet, and ii) a contact angle of the liquid droplet is measured at a timing which is 30 seconds after the liquid droplet is brought into contact with the surface.

2. The water-absorbent resin particles according to claim 1, wherein a water absorption capacity for a physiological saline solution under a load of 4.14 kPa is 15 ml/g or more.

3. The water-absorbent resin particles according to claim 1, wherein a water absorption capacity for a physiological saline solution under a load of 4.14 kPa is 18 ml/g or more.

4. The water-absorbent resin particles according to claim 1, wherein a water absorption capacity for a physiological saline solution under a load of 4.14 kPa is 20 ml/g or more.

5. The water-absorbent resin particles according to claim 1, wherein the artificial urine permeation speed when the water-absorbent resin particles are swollen tenfold is 1.0 g/min or more and 3.3 g/min or less.

6. The water-absorbent resin particles according to claim 1, wherein the water retention capacity for a physiological saline solution is 32 to 42 g/g.

7. The water-absorbent resin particles according to claim 1, wherein a water absorption speed for a physiological saline solution is 39 seconds or less.

* * * * *